United States Patent [19]
Sun et al.

[11] Patent Number: 6,051,746
[45] Date of Patent: *Apr. 18, 2000

[54] OXYGENATE CONVERSIONS USING MODIFIED SMALL PORE MOLECULAR SIEVE CATALYSTS

[75] Inventors: Hsiang-ning Sun, Houston; Stephen Neil Vaughn, Kingwood; Robert Scott Smith, Houston, all of Tex.

[73] Assignee: Exxon Chemical Patents Inc., Houston, Tex.

[ * ] Notice: This patent issued on a continued prosecution application filed under 37 CFR 1.53(d), and is subject to the twenty year patent term provisions of 35 U.S.C. 154(a)(2).

[21] Appl. No.: 08/959,673

[22] Filed: Oct. 29, 1997

Related U.S. Application Data
[60] Provisional application No. 60/050,145, Jun. 18, 1997.

[51] Int. Cl.$^7$ .................................... C07C 1/00
[52] U.S. Cl. ...................... 585/639; 585/638; 585/640
[58] Field of Search ................... 585/638, 639, 585/640

[56] References Cited

U.S. PATENT DOCUMENTS

| | | | |
|---|---|---|---|
| 4,310,440 | 1/1982 | Wilson et al. | 252/435 |
| 4,358,395 | 11/1982 | Haag et al. | 252/411 |
| 4,359,595 | 11/1982 | Rollmann | 585/640 |
| 4,440,871 | 4/1984 | Lok et al. | 502/214 |
| 4,554,143 | 11/1985 | Messina et al. | 423/306 |
| 4,554,260 | 11/1985 | Pieters et al. | 502/61 |
| 4,638,106 | 1/1987 | Pieters et al. | 585/640 |
| 4,677,242 | 6/1987 | Kaiser | 585/638 |
| 4,677,243 | 6/1987 | Kaiser | 585/638 |
| 4,732,651 | 3/1988 | Lisnyansky et al. | 162/49 |
| 4,752,651 | 6/1988 | Kaiser | 585/640 |
| 4,793,984 | 12/1988 | Lok et al. | 423/306 |
| 4,814,541 | 3/1989 | Lewis | 585/640 |
| 4,853,197 | 8/1989 | Wilson et al. | 423/306 |
| 4,861,938 | 8/1989 | Lewis et al. | 585/540 |
| 4,873,390 | 10/1989 | Lewis et al. | 585/638 |

FOREIGN PATENT DOCUMENTS

| | | |
|---|---|---|
| 9-2005496 | 9/1982 | Japan . |
| WO 93/24431 | 12/1993 | WIPO . |

OTHER PUBLICATIONS

PCT/US98/12700 International Search Report.
Zeolites, vol. 17, pp. 512–522 (1996).
Zeolites, vol. 17, pp. 212–222 (1996).
L.D. Rollmann, Mobil R&D, "Selective poisoning of ZSM–5 By Nitrogen Heterocycles", Stud. Surf. Sci, Catal. 68, 791–7 (1991).

*Primary Examiner*—Glenn Caldarola
*Assistant Examiner*—In Suk Bullock
*Attorney, Agent, or Firm*—Linda K. Russell; Bradley A. Keller

[57] ABSTRACT

The invention relates to a process for converting oxygenated organic material, to olefins using small pore molecular sieve catalysts. More particularly, the invention relates to a method for converting oxygenated organic material to olefins with improved the olefin yields and decreased yields of methane and other light saturate byproducts. The improved yield slate is achieved by treating the small pore molecular sieve catalyst with a modifier selected from the group consisting of polynuclear aromatic heterocyclic compounds with at least three interconnected ring structures having at least one nitrogen atom as a ring substituent, each ring structure having at least five ring members, decomposed derivatives of said polynuclear aromatic heterocyclic compound, and mixtures thereof.

16 Claims, No Drawings

OXYGENATE CONVERSIONS USING MODIFIED SMALL PORE MOLECULAR SIEVE CATALYSTS

This application claims priority to U.S. Provisional Patent Application No. 60/050,145, filed Jun. 18, 1997.

FIELD OF THE INVENTION

The invention relates to a process for converting oxygenated organic material to olefins using small pore molecular sieve catalysts. More particularly, the invention relates to a method for converting oxygenated organic material to olefins with improved the olefin yields and decreased yields of methane and other light saturate byproducts. The improved yield slate is achieved by treating the small pore molecular sieve catalyst with a modifier selected from the group consisting of polynuclear aromatic heterocyclic compounds with at least three interconnected ring structures having at least one nitrogen atom as a ring substituent, each ring structure having at least five ring members, decomposed derivatives of said polynuclear aromatic heterocyclic compound, and mixtures thereof.

BACKGROUND OF THE INVENTION

Light olefins, such as ethylene, serve as feeds for the production of numerous chemicals. Olefins traditionally are produced by petroleum cracking. Because of the limited supply and/or the high cost of petroleum sources, the cost of producing olefins from petroleum sources has increased steadily.

Alternative feedstocks for the production of light olefins are oxygenates, such as alcohols, particularly methanol, dimethyl ether, and ethanol. Alcohols may be produced by fermentation, or from synthesis gas derived from natural gas, petroleum liquids, carbonaceous materials, including coal, recycled plastics, municipal wastes, or any organic material. Because of the wide variety of sources, alcohol, alcohol derivatives, and other oxygenates have promise as an economical, non-petroleum source for olefin production.

The total yield slate for a typical oxygenate to olefin process includes (a) light saturates and oxygenates, i.e. methane, hydrogen, carbon monoxide, carbon dioxide, and ethane, and (b) heavier by-products with a molecular weight higher than propylene, i.e. $C_4$'s and $C_5$'s. A typical oxygenate to olefin process has a methane selectivity of no less than about 5 molar % or 2.5 wt %.

The literature related to oxygenate to olefin processes focuses on maximizing ethylene and propylene product yields. Little attention has been given to optimizing the total yield slate. One reason for this lack of attention may be that the light saturate by-products have no real fouling potential and also have some value—at least as fuel. However, it is costly to separate the light saturate by-products from the desired olefin products.

Various modifications have been made to molecular sieve catalysts having intermediate sized pores to increase the selectivity of these intermediate pore catalysts to olefins. However, little attention has been given to treatments to increase the selectivity of small pore catalysts to olefins.

Small pore zeolitic catalysts have a tendency to deactivate rapidly during the conversion of oxygenates to olefins. A need exists for methods to decrease the rate of deactivation of small pore zeolitic catalysts during such conversions.

Small pore silicoaluminophosphate (SAPO) molecular sieve catalysts have excellent selectivity in oxygenate to olefin reactions. However, a continuing need exists for treatments which will maximize the production of olefins and minimize the production of light saturate byproducts using small pore molecular sieve catalysts, generally, in order to reduce the cost of such processes and render them commercially viable.

SUMMARY OF THE INVENTION

The present invention provides a method for increasing the selectivity of a small pore molecular sieve catalyst to olefins comprising exposing said small pore molecular sieve catalyst to a modifier under conditions sufficient to produce a modified small pore molecular sieve catalyst having improved selectivity to olefins, wherein the modifier is selected from the group consisting of a polynuclear aromatic heterocyclic compound comprising at least three interconnected ring structures comprising at least one nitrogen atom as a ring substituent, each of said ring structures having at least five ring members, decomposed derivatives of said polynuclear aromatic heterocyclic compound, and mixtures thereof.

DETAILED DESCRIPTION OF THE INVENTION

Substantially any small pore molecular sieve catalyst may be modified according to the present invention. "Small pore" molecular sieve catalysts are defined herein as catalysts with pores having a diameter or pore size of less than about 5.0 Angstroms and equivalents thereof. "Equivalents thereof" is defined to refer to catalysts having a pore size that performs substantially the same function in substantially the same way to achieve substantially the same result as catalysts having a diameter or pore size of less than about 5.0 Angstroms, exclusive of catalysts having a pore size over about 5.2 Angstroms, or catalysts generally considered to be "intermediate pore" or "large pore" molecular sieve catalysts. Suitable catalysts include, but are not necessarily limited to catalysts having a pore size in the range of from about 3.8 to about 5.0 Angstroms, preferably in the range of from about 4.1 to about 5.0 Angstroms, and most preferably in the range of from about 4.3 to about 5.0 Angstroms.

Suitable small pore molecular sieve catalysts include, but are not necessarily limited to zeolites, silicoaluminophosphates (SAPOs), crystalline metal silico-aluminophosphates (MeAPSO's), crystalline metal aluminophospho oxides (MeAPO's), and aluminophospho oxides (ALPO's). Examples of suitable small pore zeolites include, but are not necessarily limited to ZSM-34, erionite, and chabazite. Examples of suitable small pore MeAPSOs and MeAPO'S include, but are not necessarily limited to SAPO's and alumino phospho oxides comprising preferably in the range of from about 0.005 to about 0.05 moles of a metal selected from the group consisting of magnesium, zinc, iron, cobalt, nickel, manganese, chromium, and mixtures thereof. Examples of suitable small pore ALPO's include, but are not necessarily limited to ALPO-17, ALPO-20, and ALPO-25. The preparation of such catalysts is well known in the art and is described in U.S. Pat. Nos. 4,554,143; 4,440,871; 4,853,197; 4,793,984, 4,752,651; and 4,310,440, all of which are incorporated herein by reference. Preferred molecular sieve catalysts are SAPOs, such as SAPO-34, SAPO 17, SAPO-18, SAPO-43, and SAPO-44, and others which may be synthesized according to U.S. Pat. No. 4,440,871, incorporated herein by reference, and *Zeolites*, Vol. 17, pp. 512–522 (1996), incorporated herein by reference. Most preferred catalysts are SAPO-17, SAPO-18, and SAPO-34.

SAPO's have a three-dimensional microporous crystal framework of $PO^+$, $AlO_2^-$, and $SiO_2$ tetrahedral units. The chemical composition (anhydrous) is:

wherein "R" represents at least one organic templating agent present in the intracrystalline pore system: "m" represents the moles of "R" present per mole of $(Si_xAl_yP_z)O_2$ and has a value of from zero to 0.3, the maximum value in each case depending upon the molecular dimensions of the templating agent and the available void volume in the pore system of the particular SAPO species involved, and "x", "y", and "z" represent the mole fractions of silicon, aluminum and phosphorus, respectively. "R" may be removed at elevated temperatures.

The modifiers of the present invention comprise polynuclear aromatic heterocyclic compounds with at least three interconnected ring structures having at least one nitrogen atom as a ring substituent, each ring structure having at least five ring members, and quaternary salts thereof. Suitable modifiers include, but are not necessarily limited to compositions having the following general structure:

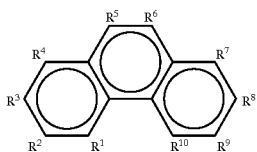

wherein at least one of $R^1$–$R^{10}$ is nitrogen. In a preferred embodiment, two of $R^1$–$R^{10}$ are nitrogens. In a most preferred embodiment, two nitrogens are substituents on the ring at positions selected from the group consisting of $R^1$ and $R^{10}$, $R^4$ and $R^7$, $R^1$ and $R^7$, and $R^5$ and $R^6$. Examples include 1,10-phenanthroline, 4,7-phenanthroline, 1,7-phenanthroline, and benzo(c)cinnoline. A preferred modifier having the foregoing structure is 1,10-phenanthroline, in which $R^1$ and $R^{10}$ are nitrogens.

Suitable modifiers also include, but are not necessarily limited to compositions having the following general structure, and quaternary salts thereof:

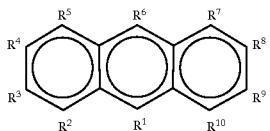

wherein at least one of $R^1$–$R^{10}$ is nitrogen, preferably two of $R^1$–$R^{10}$ are nitrogens. In a most preferred embodiment, $R^1$ and $R^6$ are nitrogens, resulting in phenazine.

The modifiers of the present invention may be adsorbed onto the catalyst either prior to or simultaneous with the introduction of the oxygenate feed.

The modifier may be adsorbed onto the catalyst prior to the introduction of the feed using any suitable means. In one embodiment, a solution of the desired modifier is first made by dissolving a desired amount of the modifier in a solvent under mild conditions. Suitable solvents are organic, inorganic, and aqueous. If water is used, the water preferably should be de-ionized. Adjusting the pH to below 7.0 in an aqueous system also helps the dissolution of the modifiers. The temperature of mixing is dependent upon the solubility of the modifier in the solvent selected. The process may be conducted under pressure, at reduced pressure, or at atmospheric pressure.

After adequate mixing, the solution is added to a predetermined amount of the catalyst. The resulting mixture is stirred as required. In some cases, stirring is not required and the mixture may be left undisturbed for a time adequate to permit the desired level of modifier adsorption onto the catalyst. The catalyst product then is filtered and dried. The catalyst preferably is then calcined to decompose at least a portion of the modifier in an essentially non-oxidizing atmosphere by methods well known to those skilled in the art. Suitable non-oxidizing atmospheres include, but are not necessarily limited to nitrogen, argon, helium, carbon dioxide, etc.

The amount of modifier adsorbed onto the catalyst may vary over a wide range depending, at least in part, on the selected catalyst and the incorporation method. Preferably, the amount of the modifier adsorbed should be at least about 0.0001 wt. %, most preferably in the range of from about 0.001 wt. % and about 5.0 wt. % nitrogen.

If the modifier is to be introduced with the oxygenate feed, the modifier may be injected into the system in any suitable manner as long as the conditions are such that the modifier is miscible with the feed. For example, if the modifier has a low solubility in alcohol, the solubility limits should not be exceeded. Or, if the modifier has an exceptionally high melting or boiling point, suitable adjustments should be made. If the reaction is carried out in the vapor phase, a modifier with a boiling point below the process temperature preferably should be used so that the modifier may be carried into the reactor by entrainment, downflow, or other methods known to those skilled in the art.

The conversion process employs an organic starting material (feedstock) preferably comprising "oxygenates". As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety preferably should contain in the range of from about 1–10 carbon atoms and more preferably in the range of from about 1–4 carbon atoms. Representative oxygenates include, but are not necessarily limited to, lower straight chain or branched aliphatic alcohols, their unsaturated counterparts, and their nitrogen, halogen and sulfur analogues. Examples of suitable compounds include, but are not necessarily limited to: methanol; ethanol; n-propanol; isopropanol; $C_4$–$C_{10}$ alcohols; methyl ethyl ether; dimethyl ether; diethyl ether; di-isopropyl ether; methyl mercaptan; methyl sulfide; methyl amine; ethyl mercaptan; diethyl sulfide; diethyl amine; ethyl chloride; formaldehyde; dimethyl carbonate; dimethyl ketone; acetic acid; n-alkyl amines, n-alkyl halides, n-alkyl sulfides having n-alkyl groups of in the range of from about 3–10 carbon atoms; and mixtures thereof. As used herein, the term "oxygenate" designates only the organic material used as the feed. The total charge of feed to the reaction zone may contain additional compounds such as diluents.

The conversion of feed to olefins preferably should be carried out in the vapor phase. Preferably, the feedstock should be contacted in the vapor phase in a reaction zone with the defined molecular sieve catalyst at effective process conditions so as to produce the desired olefins, i.e., an effective temperature, pressure, WHSV (Weight Hourly Space Velocity) and, optionally, an effective amount of diluent, correlated to produce olefins. Alternately, the process may be carried out in a liquid phase. When the process is carried out in the liquid phase, different conversion rates and selectivities of feedstock-to-product may result depending upon the composition of the liquid.

The temperature employed in the conversion process may vary over a wide range depending, at least in part, on the selected catalyst. Although not limited to a particular temperature, best results will be obtained if the process is conducted at temperatures in the range of from about 200° C. to about 700° C., preferably in the range of from about 250° C. to about 600° C., and most preferably in the range of from about 300° C. to about 500° C. Lower temperatures generally result in lower rates of reaction, and the formation of the desired light olefin products may become markedly slow. However, at higher temperatures, the process may not form an optimum amount of light olefin products, and the coking rate may become too high.

Light olefin products will form—although not necessarily in optimum amounts—at a wide range of pressures, including but not limited to autogeneous pressures and pressures in the range of from about 0.1 kPa to about 100 MPa. A preferred pressure is in the range of from about 6.9 kPa to about 34 MPa, most preferably in the range of from about 48 kPa to about 0.34 MPa. The foregoing pressures are exclusive of diluent, if any is present, and refer to the partial pressure of the feedstock as it relates to oxygenate compounds and/or mixtures thereof. Pressures outside of the stated ranges may operate and are not excluded from the scope of the invention. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor), and the selected process design characteristics.

A wide range of weight hourly space velocity (WHSV) for the feedstock will function in the present invention. The WHSV generally should be in the range of from about 0.01 $hr^{-1}$ to about 500 $hr^{-1}$, preferably in the range of from about 0.1 $hr^{-1}$ to about 200 $hr^{-1}$, and most preferably in the range of from about 0.5 $hr^{-1}$ to about 100 $hr^{-1}$. The catalyst may contain other materials which act as inerts, fillers, or binders; therefore, the WHSV is calculated on the weight basis of methanol or dimethyl ether and catalyst.

The feed may contain one or more diluents in an amount in the range of from about 1 and 99 molar percent, based on the total number of moles of all feed and diluent components fed to the reaction zone (or catalyst). Diluents which may be employed in the process include, but are not necessarily limited to, helium, argon, nitrogen, carbon monoxide, carbon dioxide, hydrogen, water, paraffins, other hydrocarbons (such as methane), aromatic compounds, and mixtures thereof. Preferred diluents are water and nitrogen.

The process may be carried out in a batch, semi-continuous, or continuous fashion. The process may use a single reaction zone or a number of reaction zones arranged in series or in parallel. The process may be intermittent or continuous in an elongated tubular zone or a number of such zones. When multiple reaction zones are used, one or more of the small pore catalysts advantageously may be used in series to provide for a desired product mixture.

A dynamic bed system, or any system that includes a variety of transport beds rather than fixed beds, may be desirable. If regeneration of the catalyst is required, such a system would permit introduction of the catalyst as a moving bed to a regeneration zone where, e.g., carbonaceous material could be removed or oxidized. Preferably, the catalyst should be regenerated by burning off carbonaceous deposits that accumulate during the process.

The following examples illustrate, but do not limit, the present invention.

EXAMPLE I

A sample of SAPO-34 was obtained from UOP, Des Plaines, Ill., disclosed in U.S. Pat. No. 4,440,871, incorporated herein by reference.

EXAMPLE II

Two samples of 5.0 cc (approximately 2.7 grams) of the catalyst obtained in Example I were mixed with 15 cc of quartz beads and loaded into 1.9 cm (¾inch) outer diameter 316 stainless steel tubular reactors which were heated by three-zone electric furnaces. The first zone, acting as the preheating zone, vaporized the feed. The temperature of the center zone of the furnace was adjusted to 450° C. and the pressure was maintained at 100 kPa (1 atm). The reactor was purged first with nitrogen at 50 cc/min flow rate for 30 minutes. The feed for Reactor A was a 4:1 (molar ratio) of water and methanol (control). The feed for Reactor B was the same with the addition of 100 ppm 1,10-phenanthroline. The feeds were pumped into the reactors and calibrated to give a flow rate of about 0.7 $hr^{-1}$ WHSV. The effluent was analyzed at pre-determined intervals by an on-line gas chromatograph fitted with both a thermal conductivity detector and a flame ionization detector.

The results are shown in the following table.

| Yield, Wt. % | Reactor A | Reactor B |
| --- | --- | --- |
| Methane | 4 | 2.2 |
| Ethylene | 49.2 | 52.2 |
| Propylene | 34 | 32.6 |

The modified SAPO-34 catalyst exhibited an increase of approximately 3% in ethylene yield, and decreases of approximately 1.8% and 1.4% in methane yield and propylene yield, respectively.

EXAMPLE III 0.31 grams of phenazine is dissolved in 50 cc of pure ethanol at 60° C. The solution is added to 5.2 grams of the catalyst prepared in Example I. The resulting mixture is stirred and left undisturbed for 24 hours. The catalyst product then is filtered, dried, and calcined under nitrogen atmosphere for 16 hours at 550° C. The mixture is allowed to stand at room temperature for one hour, and then dried at 110° C. for 2 hours. The resulting dried catalyst is then calcined under nitrogen atmosphere at 500° C. for 16 hours, to result in modified SAPO-34.

EXAMPLE IV

The control and the modified catalyst prepared in Example III are tested using the following procedure. 5.0 cc (approximately 2.7 grams) of each catalyst is diluted with 15 cc of glass beads and loaded into a 1.9 cm (¾inch), outer diameter 316 stainless steel tubular reactor which is heated by a three-zone electric furnace. The first zone, acting as the preheating zone, vaporizes the feed. The temperature of the center zone of the furnace is adjusted to give a reaction temperature of 450° C. and the pressure is maintained at 100 kPa (1 atm). The reactor is purged first with nitrogen at 50 cc/min flow rate for 30 minutes. The feed, a 4:1 (molar ratio) of water and methanol, is pumped into the reactor and calibrated to give a flow rate of about 0.7 hr$^{-1}$ WHSV calculated on the basis of methanol and catalyst only. The effluent is analyzed at pre-determined intervals by an on-line gas chromatograph fitted with both a thermal conductivity detector and a flame ionization detector.

The results are substantially the same as in Example II.

Persons of ordinary skill in the art will recognize that many modifications may be made to the present invention without departing from the spirit and scope of the present invention. The embodiments described herein are meant to be illustrative only and should not be taken as limiting the invention, which is defined in the following claims.

We claim:

1. A method for converting an organic starting material including at least one oxygenate to olefins comprising:
    contacting a feed comprising said organic starting material including at least one oxygenate with a small pore molecular sieve catalyst other than a zeolite under conditions effective to produce olefins, wherein said catalyst comprises a framework of material selected from the group consisting of silica, alumina, phosphate, and combinations thereof, and a modifier selected from the group consisting of:
        polynuclear aromatic heterocyclic compounds comprising at least three interconnected ring structures comprising at least one nitrogen atom as a ring substituent, each of said ring structures having at least five ring members;
        decomposed derivatives of said polynuclear aromatic heterocyclic compounds; and
        mixtures thereof.

2. The method of claim 1 wherein said polynuclear aromatic heterocyclic compounds have the following general structure:

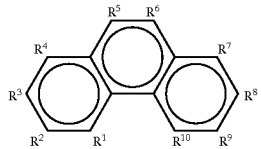

wherein at least one of R$^1$–R$^{10}$ comprises nitrogen.

3. The method of claim 2 wherein at least two of R$^1$–R$^{10}$ comprise nitrogen.

4. The method of claim 2 wherein said polynuclear aromatic heterocyclic compounds comprise at least two nitrogen ring substituents at positions selected from the group consisting of R$^1$ and R$^{10}$, R$^4$ and R$^7$, R$^1$ and R$^7$, and R$^5$ and R$^6$.

5. The method of claim 1 wherein said polynuclear aromatic heterocyclic compound comprises 1,10-phenanthroline.

6. The method of claim 1 wherein said polynuclear aromatic heterocyclic compounds have the following general structure:

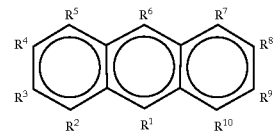

wherein at least one of R$^1$–R$^{10}$ is nitrogen.

7. The method of claim 6 wherein two of R$^1$–R$^{10}$ are nitrogens.

8. The method of claim 6 wherein said polynuclear aromatic heterocyclic compound comprises phenazine.

9. The method of claim 1 wherein said catalyst is a silicoaluminophosphate catalyst comprising pores consisting essentially of a diameter less than about 5.0 Angstroms.

10. The method of claim 2 wherein said catalyst is a silicoaluminophosphate catalyst comprising pores consisting essentially of a diameter less than about 5.0 Angstroms.

11. The method of claim 4 wherein said catalyst is a silicoaluminophosphate catalyst comprising pores consisting essentially of a diameter less than about 5.0 Angstroms.

12. The method of claim 5 wherein said catalyst is a silicoaluminophosphate catalyst comprising pores consisting essentially of a diameter less than about 5.0 Angstroms.

13. The method of claim 6 wherein said catalyst is a silicoaluminophosphate catalyst comprising pores consisting essentially of a diameter less than about 5.0 Angstroms.

14. The method of claim 7 wherein said catalyst is a silicoaluminophosphate catalyst comprising pores consisting essentially of a diameter less than about 5.0 Angstroms.

15. The method of claim 8 wherein said catalyst is a silicoaluminophosphate catalyst comprising pores consisting essentially of a diameter less than about 5.0 Angstroms.

16. The method of claim 1 wherein said organic starting material is selected from the group consisting of methanol and dimethyl ether.

* * * * *

UNITED STATES PATENT AND TRADEMARK OFFICE
CERTIFICATE OF CORRECTION

PATENT NO. : 6,051,746  
DATED : April 18, 2000  
INVENTOR(S) : Hsiang-ning Sun, Neil Vaughn, Robert Scott Smith Page 1 of 1

It is certified that error appears in the above-identified patent and that said Letters Patent is hereby corrected as shown below:

Abstract,
Line 5, replace "with improved" with -- which improves --.

Column 1,
Line 13, replace "with improved" with -- which improves --.

Column 6,
Line 59, Punctuation after "procedure" is not correct. Replace "procedure." with "procedure;"

Signed and Sealed this

Twenty-fifth Day of September, 2001

Attest:

*Attesting Officer*

NICHOLAS P. GODICI  
*Acting Director of the United States Patent and Trademark Office*